(12) United States Patent
Kassab

(10) Patent No.: US 9,289,229 B2
(45) Date of Patent: *Mar. 22, 2016

(54) DEVICES AND METHODS FOR REMOVING STENOTIC LESIONS FROM VESSELS

(71) Applicant: 3DT Holdings, LLC, Zionsville, IN (US)

(72) Inventor: Ghassan S. Kassab, Zionsville, IN (US)

(73) Assignee: 3DT Holdings, LLC, San Diego, CA (US)

( * ) Notice: Subject to any disclaimer, the term of this patent is extended or adjusted under 35 U.S.C. 154(b) by 35 days.

This patent is subject to a terminal disclaimer.

(21) Appl. No.: 13/920,833

(22) Filed: Jun. 18, 2013

(65) Prior Publication Data

US 2013/0282037 A1 Oct. 24, 2013

Related U.S. Application Data

(60) Continuation of application No. 12/428,656, filed on Apr. 23, 2009, now Pat. No. 8,465,452, which is a continuation-in-part of application No. 12/098,242, filed on Apr. 4, 2008, now Pat. No. 8,078,274, which is (Continued)

(51) Int. Cl.
*A61M 29/00* (2006.01)
*A61B 17/3207* (2006.01)
(Continued)

(52) U.S. Cl.
CPC ............. *A61B 17/3207* (2013.01); *A61B 5/053* (2013.01); *A61B 5/0538* (2013.01);
(Continued)

(58) Field of Classification Search
CPC .................................................. A61B 17/3207

USPC ......... 600/547, 587, 393, 439, 114, 117, 470; 606/21, 127, 159; 33/512; 29/25.35; 623/1.11
See application file for complete search history.

(56) References Cited

U.S. PATENT DOCUMENTS 3,896,373 A 7/1975 Zelby
4,380,237 A 4/1983 Newbower
(Continued)

FOREIGN PATENT DOCUMENTS

EP 1 025 805 A1 8/2000
WO WO 98/35611 A1 8/1998
(Continued)

OTHER PUBLICATIONS

International Searching Authority, International Search Report, dated Jul. 6, 2005 (PCT/US04/04828).
(Continued)

*Primary Examiner* — Brian Szmal
(74) *Attorney, Agent, or Firm* — Reichel Stohry LLP; Michael C. Reichel; Natalie J. Dean

(57) ABSTRACT

The present application provides various devices, systems, and methods for removing stenotic lesions from vessels. In at least one embodiment of an exemplary device of the present disclosure, the device comprises at least one treatment portion operable to remove at least part of a stenotic lesion, and at least one sizing portion operable to measure a first luminal size parameter when positioned and operated at a first location and further operable to measure a second luminal size parameter when positioned and operated at a second location, wherein the device comprises an elongated body selected from the group consisting of a catheter and a wire.

18 Claims, 9 Drawing Sheets

Related U.S. Application Data a continuation-in-part of application No. 11/891,981, filed on Aug. 14, 2007, now Pat. No. 8,114,143, which is a division of application No. 10/782,149, filed on Feb. 19, 2004, now Pat. No. 7,454,244.

(60) Provisional application No. 60/449,266, filed on Feb. 21, 2003, provisional application No. 60/493,145, filed on Aug. 7, 2003, provisional application No. 60/502,139, filed on Sep. 11, 2003.

(51) Int. Cl.
| | |
|---|---|
| A61B 5/053 | (2006.01) |
| A61B 5/107 | (2006.01) |
| A61B 17/22 | (2006.01) |
| A61B 18/02 | (2006.01) |
| A61B 18/24 | (2006.01) |
| A61B 17/00 | (2006.01) |
| A61B 18/00 | (2006.01) |
| A61F 2/958 | (2013.01) |

(52) U.S. Cl.
CPC ......... *A61B5/1076* (2013.01); *A61B 17/22004* (2013.01); *A61B 17/320725* (2013.01); *A61B 17/320758* (2013.01); *A61B 18/02* (2013.01); *A61B 18/24* (2013.01); *A61B 2017/00026* (2013.01); *A61B 2017/22044* (2013.01); *A61B 2017/22061* (2013.01); *A61B 2018/0022* (2013.01); *A61B 2018/0212* (2013.01); *A61F 2/958* (2013.01)

(56) References Cited

U.S. PATENT DOCUMENTS

| | | | |
|---|---|---|---|
| 4,587,975 A | | 5/1986 | Salo et al. |
| 4,840,182 A | | 6/1989 | Carlson |
| 4,841,977 A | * | 6/1989 | Griffith et al. ............... 600/439 |
| 4,873,987 A | | 10/1989 | Djordjevich et al. |
| 4,957,110 A | | 9/1990 | Vogel et al. |
| 5,058,583 A | | 10/1991 | Geddes et al. |
| 5,125,410 A | | 6/1992 | Misono et al. |
| 5,233,994 A | | 8/1993 | Shmulewitz |
| 5,366,443 A | | 11/1994 | Eggers et al. |
| 5,453,576 A | | 9/1995 | Krivitski |
| 5,665,103 A | | 9/1997 | Lafontaine et al. |
| 5,827,192 A | | 10/1998 | Gopakumaran et al. |
| 5,842,998 A | | 12/1998 | Gopakumaran et al. |
| 5,971,933 A | | 10/1999 | Schluter et al. |
| 6,081,737 A | * | 6/2000 | Shah ............................ 600/393 |
| 6,112,115 A | | 8/2000 | Feldman et al. |
| 6,165,977 A | | 12/2000 | Mochly-Rosen |
| 6,187,744 B1 | | 2/2001 | Rooney |
| 6,191,136 B1 | | 2/2001 | Marban |
| 6,270,493 B1 | | 8/2001 | Lalonde et al. |
| 6,296,615 B1 | | 10/2001 | Brockway et al. |
| 6,325,762 B1 | | 12/2001 | Tjin |
| 6,354,999 B1 | | 3/2002 | Dgany et al. |
| 6,360,123 B1 | | 3/2002 | Kimchi |
| 6,398,738 B1 | | 6/2002 | Millar |
| 6,406,422 B1 | | 6/2002 | Landesberg |
| 6,471,656 B1 | | 10/2002 | Shalman et al. |
| 6,494,832 B1 | | 12/2002 | Feldman et al. |
| 6,511,413 B2 | | 1/2003 | Landesberg |
| 6,569,862 B1 | | 5/2003 | Marban |
| 6,652,505 B1 | | 11/2003 | Tsugita |
| 6,663,661 B2 | | 12/2003 | Boneau |
| 6,666,828 B2 | | 12/2003 | Greco et al. |
| 6,926,674 B2 | | 8/2005 | Tenerz et al. |
| 6,939,313 B2 | | 9/2005 | Saadat |
| 7,069,072 B2 | | 6/2006 | Jansen et al. |
| 7,141,019 B2 | | 11/2006 | Pearlman |
| 7,169,107 B2 | | 1/2007 | Jersey-Willuhn et al. |
| 7,189,208 B1 | | 3/2007 | Beatty et al. |
| 7,236,820 B2 | | 6/2007 | Mabary et al. |
| 7,311,702 B2 | | 12/2007 | Tallarida et al. |
| 7,326,241 B2 | | 2/2008 | Jang |
| 7,454,244 B2 | | 11/2008 | Kassab et al. |
| 8,078,274 B2 | * | 12/2011 | Kassab ........................ 600/547 |
| 8,465,452 B2 | * | 6/2013 | Kassab ..................... 604/95.01 |
| 2002/0049488 A1 | | 4/2002 | Boneau |
| 2002/0062149 A1 | | 5/2002 | Jang |
| 2002/0177783 A1 | | 11/2002 | Khalil |
| 2003/0013986 A1 | | 1/2003 | Saadat |
| 2004/0044286 A1 | | 3/2004 | Hossack et al. |
| 2004/0116816 A1 | | 6/2004 | Tenerz et al. |
| 2004/0243116 A1 | | 12/2004 | Joye et al. |
| 2004/0254495 A1 | | 12/2004 | Mabary et al. |
| 2010/0222786 A1 | | 9/2010 | Kassab |

FOREIGN PATENT DOCUMENTS

| | | |
|---|---|---|
| WO | WO 02/19905 | 3/2002 |
| WO | WO 02/085442 A1 | 10/2002 |
| WO | WO 03/092495 A1 | 11/2003 |

OTHER PUBLICATIONS

International Searching Authority, Written Opinion, dated Jul. 6, 2005 (PCT/US04/04828).
International Searching Authority, International Search Report, dated Aug. 8, 2007 (PCT/US06/05985).
International Searching Authority, Written Opinion, dated Aug. 8, 2007 (PCT/US06/05985).
Supplemental European Search Report for EP 04 71 2383 to Electro-Cat, LLC dated Aug. 6, 2007.
International Searching Authority, Written Opinion, dated Jun. 28, 2010 (PCT/US2010/031553).
International Searching Authority, International Preliminary Report on Patentability, dated Nov. 3, 2011 (PCT/US2010/032178).
Hoekstein and Inbar, "Cardiac Stroke Volume Estimation from . . . Measurements." Technion Department of Electrical Engineering Publication EE PUB No. 911, Feb. 1994.
Kornet, et al., "Conductance Method for the Measurement of . . . Conductance," Annals of Biomedical Engineering, vol. 27, pp. 141-150, 1999.
Hettrick, et al., "Finite Element Model . . . via Conductance," Annals of Biomedical Engineering, vol. 27, pp. 151-159, 1999.
Hettrick, et al., "In Vivo Measurement of Real-Time Aortic Segmental Volume Using toe Conductance Catheter," Annals of Biomedical Engineering, vol. 26, pp. 431-440, 1999.

* cited by examiner

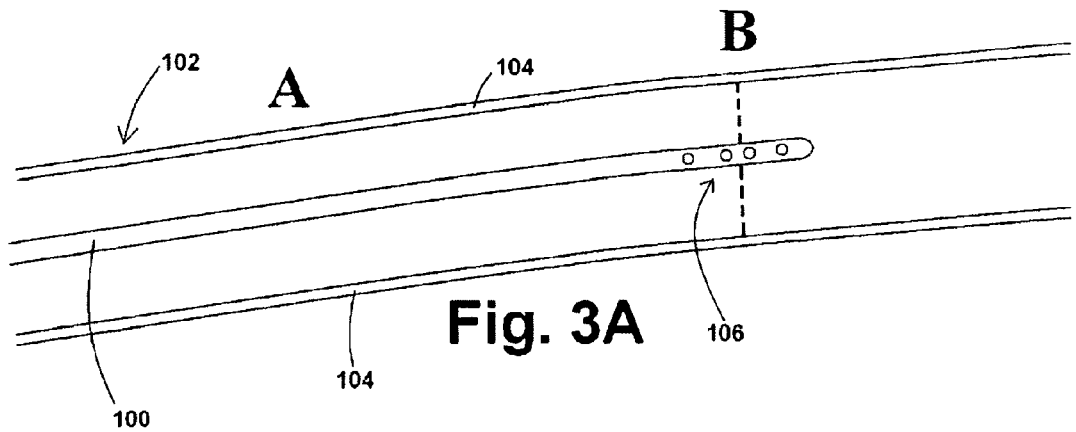
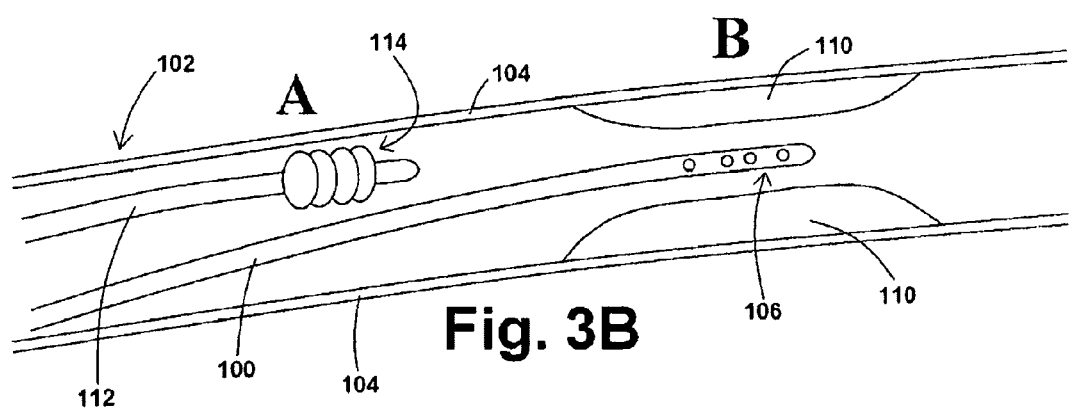
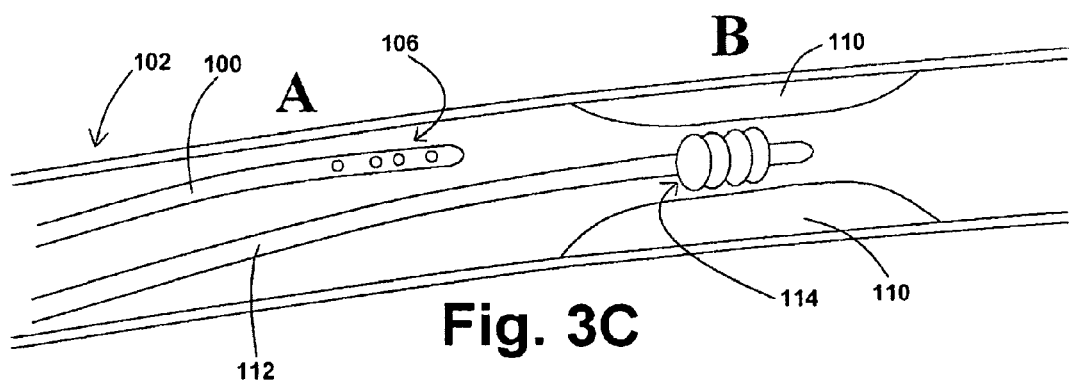

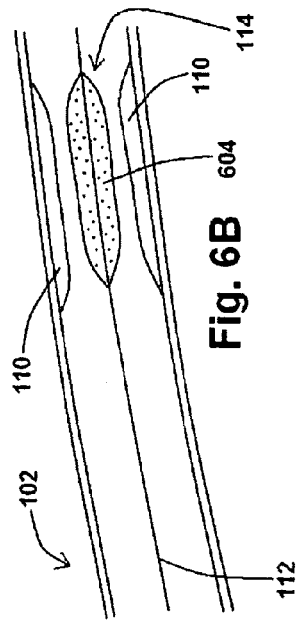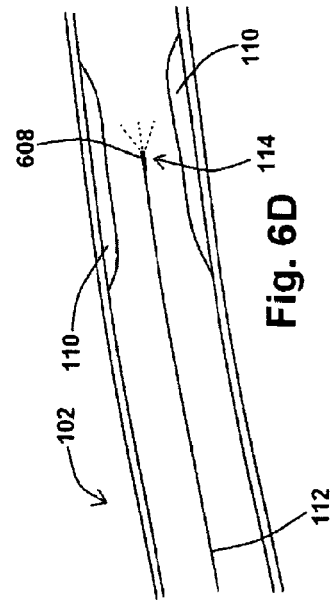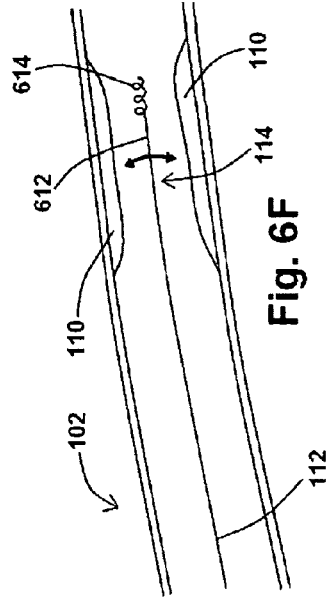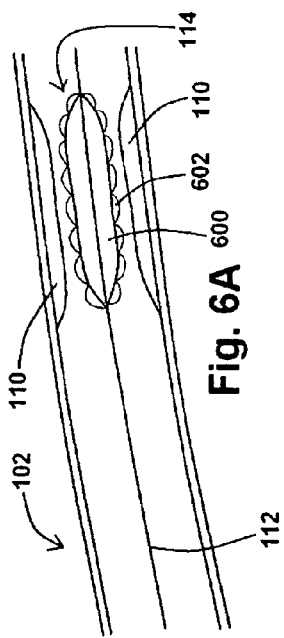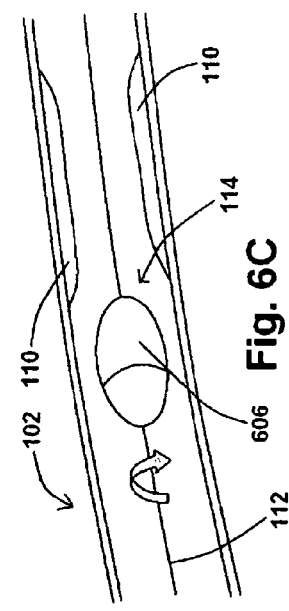

DEVICES AND METHODS FOR REMOVING STENOTIC LESIONS FROM VESSELS

PRIORITY

The present application is related to, claims the priority benefit of, and is a continuation application of, U.S. patent application Ser. No. 12/428,656, filed Apr. 23, 2009 and issued as U.S. Pat. No. 8,465,452 on Jun. 18, 2013, which is related to, claims the priority benefit of, and is a continuation-in-part application of, U.S. patent application Ser. No. 12/098,242, filed Apr. 4, 2008 and issued as U.S. Pat. No. 8,078,274 on Dec. 13, 2011, which is related to, claims the priority benefit of, and is a continuation-in-part application of, U.S. patent application Ser. No. 11/891,981, filed Aug. 14, 2007 and issued as U.S. Pat. No. 8,114,143 on Feb. 14, 2012, which is related to, claims the priority benefit of, and is a divisional application of, U.S. patent application Ser. No. 10/782,149, filed Feb. 19, 2004 and issued as U.S. Pat. No. 7,454,244 on Nov. 18, 2008, which is related to, and claims the priority benefit of, (a) U.S. Provisional Patent Application Ser. No. 60/449,266, filed Feb. 21, 2003, (b) U.S. Provisional Patent Application Ser. No. 60/493,145, filed Aug. 7, 2003, and (c) U.S. Provisional Patent Application Ser. No. 60/502,139, filed Sep. 11, 2003. The contents of each of these applications and patents are hereby incorporated by reference in their entirety into this disclosure.

BACKGROUND

The disclosure of the present application relates generally to devices, systems, and methods for removing stenotic lesions from vessels. In at least one embodiment, the disclosure of the present application relates to methods for removing stenotic lesions from vessels involving obtaining one or more luminal size parameters of blood vessels, heart valves and other hollow visceral organs.

Coronary Heart Disease

Coronary heart disease is caused by atherosclerotic narrowing of the coronary arteries. It is likely to produce angina pectoris, heart attack or both. Coronary heart disease caused 466,101 deaths in USA in 1997 and is the single leading cause of death in America today. Approximately, 12 million people alive today have a history of heart attack, angina pectoris or both. The break down for males and females is 49% and 51%, respectively. This year, an estimated 1.1 million Americans will have a new or recurrent coronary attack, and more than 40% of the people experiencing these attacks will die as a result. About 225,000 people a year die of coronary attack without being hospitalized. These are sudden deaths caused by cardiac arrest, usually resulting from ventricular fibrillation. More than 400,000 Americans and 800,000 patients world-wide undergo a non-surgical coronary artery interventional procedure each year. Although only introduced in the 1990s, in some laboratories intra-coronary stents are used in 90% of these patients.

Stents increase minimal coronary lumen diameter to a greater degree than percutaneous transluminal coronary angioplasty (PTCA) alone according to the results of two randomized trials using the Palmaz-Schatz stent. These trials compared two initial treatment strategies: stenting alone and PTCA with "stent backup" if needed. In the STRESS trial, there was a significant difference in successful angiographic outcome in favor of stenting (96.1% vs. 89.6%).

Aortic Stenosis

Aortic Stenosis (AS) is one of the major reasons for valve replacements in adult. AS occurs when the aortic valve orifice narrows secondary to valve degeneration. The aortic valve area is reduced to one fourth of its normal size before it shows a hemodynamic effect. Because the area of the normal adult valve orifice is typically 3.0 to 4.0 $cm^2$, an area 0.75-1.0 $cm^2$ is usually not considered severe AS. When stenosis is severe and cardiac output is normal, the mean trans-valvular pressure gradient is generally >50 mmHg. Some patients with severe AS remain asymptomatic, whereas others with only moderate stenosis develop symptoms. Therapeutic decisions, particularly those related to corrective surgery, are based largely on the presence or absence of symptoms.

The natural history of AS in the adult consists of a prolonged latent period in which morbidity and mortality are very low. The rate of progression of the stenotic lesion has been estimated in a variety of hemodynamic studies performed largely in patients with moderate AS. Cardiac catheterization and Doppler echocardiographic studies indicate that some patients exhibit a decrease in valve area of 0.1-0.3 $cm^2$ per year; the average rate of change is 0.12 $cm^2$ per year. The systolic pressure gradient across the valve may increase by as much as 10 to 15 mmHg per year. However, more than half of the reported patients showed little or no progression over a 3-9 year period. Although it appears that progression of AS can be more rapid in patients with degenerative calcific disease than in those with congenital or rheumatic disease, it is not possible to predict the rate of progression in an individual patient.

Eventually, symptoms of angina, syncope, or heart failure develop after a long latent period, and the outlook changes dramatically. After onset of symptoms, average survival is <2-3 years. Thus, the development of symptoms identifies a critical point in the natural history of AS.

Many asymptomatic patients with severe AS develop symptoms within a few years and require surgery. The incidence of angina, dyspnea, or syncope in asymptomatic patients with Doppler outflow velocities of 4 m/s has been reported to be as high as 38% after 2 years and 79% after 3 years. Therefore, patients with severe AS require careful monitoring for development of symptoms and progressive disease.

Indications for Cardiac Catheterization

In patients with AS, the indications for cardiac catheterization and angiography are to assess the coronary circulation (to confirm the absence of coronary artery disease) and to confirm or clarify the clinical diagnosis of AS severity. If echocardiographic data are typical of severe isolated. AS, coronary angiography may be all that is needed before aortic valve replacement (AVR). Complete left- and right-heart catheterization may be necessary to assess the hemodynamic severity of AS if there is a discrepancy between clinical and echocardiographic data or evidence of associated valvular or congenital disease or pulmonary hypertension.

The pressure gradient across a stenotic valve is related to the valve orifice area and transvalvular flow through Bernoulli's principle. Thus, in the presence of depressed cardiac output, relatively low pressure gradients are frequently obtained in patients with severe AS. On the other hand, during exercise or other high-flow states, systolic gradients can be measured in minimally stenotic valves. For these reasons, complete assessment of AS requires (1) measurement of transvalvular flow, (2) determination of the transvalvular pressure gradient, and (3) calculation of the effective valve area. Careful attention to detail with accurate measurements of pressure and flow is important, especially in patients with low cardiac output or a low transvalvular pressure gradient.

Problems with Current Aortic Valve Area Measurements

Patients with severe AS and low cardiac output are often present with only modest transvalvular pressure gradients (i.e., <30 mmHg). Such patients can be difficult to distinguish from those with low cardiac output and only mild to moderate AS. In both situations, the low-flow state and low pressure gradient contribute to a calculated effective valve area that can meet criteria for severe AS. The standard valve area formula (simplified Hakki formula which is valve area=cardiac output/[pressure gradient]$^{1/2}$) is less accurate and is known to underestimate the valve area in low-flow states; under such conditions, it should be interpreted with caution. Although valve resistance is less sensitive to flow than valve area, resistance calculations have not been proved to be substantially better than valve area calculations.

In patients with low gradient stenosis and what appears to be moderate to severe AS, it may be useful to determine the transvalvular pressure gradient and calculate valve area and resistance during a baseline state and again during exercise or pharmacological (i.e., dobutamine infusion) stress. Patients who do not have true, anatomically severe stenosis exhibit an increase in the valve area during an increase in cardiac output. In patients with severe AS, these changes may result in a calculated valve area that is higher than the baseline calculation but that remains in the severe range, whereas in patients without severe AS, the calculated valve area will fall outside the severe range with administration of dobutamine and indicate that severe AS is not present.

There are many other limitations in estimating aortic valve area in patients with aortic stenosis using echocardiography and cardiac catheterization. Accurate measurement of the aortic valve area in patients with aortic stenosis can be difficult in the setting of low cardiac output or concomitant aortic or mitral regurgitations. Concomitant aortic regurgitation or low cardiac output can overestimate the severity of aortic stenosis. Furthermore, because of the dependence of aortic valve area calculation on cardiac output, any under or overestimation of cardiac output will cause inaccurate measurement of valve area. This is particularly important in patients with tricuspid regurgitation. Falsely measured aortic valve area could cause inappropriate aortic valve surgery in patients who do not need it.

Other Visceral Organs

Visceral organs such as the gastrointestinal tract and the urinary tract serve to transport luminal contents (fluids) from one end of the organ to the other end or to an absorption site. The esophagus, for example, transports swallowed material from the pharynx to the stomach. Diseases may affect the transport function of the organs by changing the luminal cross-sectional area, the peristalsis generated by muscle, or by changing the tissue components. For example, strictures in the esophagus and urethra constitute a narrowing of the organ where fibrosis of the wall may occur. Strictures and narrowing can be treated with distension, much like the treatment of plaques in the coronary arteries.

As referenced in detail above, and given the prevalence of coronary heart disease and its potential severe prognosis, the availability of various devices, systems, and methods for removing stenotic lesions from vessels in an effective fashion would be well-received by the public, including treating physicians. The disclosure of the present application provides effective devices, systems, and methods useful to remove stenotic lesions and overcome known problems regarding current treatment devices and methods and the current lack of effective devices and methods to perform the same.

BRIEF SUMMARY

In at least one exemplary method for removing a stenotic lesion of a vessel of the present disclosure, the method comprises the steps of measuring a first luminal size parameter at a first location within a vessel lumen, measuring a second luminal size parameter at a second location within the vessel lumen, determining a preferred second luminal size parameter based upon the first luminal size parameter and the second luminal size parameter, and positioning a treatment device to at or near the second location. In at least one method, the method further comprises the steps of operating the treatment device to increase the second luminal size parameter and measuring a then-current luminal size parameter at the second location. After the then-current luminal size parameter at the second location is measured, an exemplary method for removing a stenotic lesion of a vessel comprises the step of comparing the then-current luminal size parameter to the preferred second luminal size parameter, and if the then-current luminal size parameter does not equal the preferred second luminal size parameter, an exemplary method comprises repeating the steps of operating the treatment device to increase the second luminal size parameter, measuring another then-current luminal size parameter at the second location, and comparing the then-current luminal size parameter to the preferred second luminal size parameter. In at least one embodiment of such a method, the aforementioned three steps are repeated until the then-current luminal size parameter equals the preferred second luminal size parameter.

In at least one exemplary system for removing a stenotic lesion of a vessel of the present disclosure, the system comprises a treatment device, the treatment device comprising at least one treatment portion operable to remove at least part of a stenotic lesion, and a sizing device, the sizing device comprising electrodes operable to measure a first luminal size parameter when the sizing device is positioned at a first location, and wherein the sizing device is further operable to measure a second luminal size parameter when the sizing device is positioned at a second location.

In at least one exemplary method for removing a stenotic lesion of a vessel of the present disclosure, the method comprises the steps of positioning a device within a vessel lumen, the device comprising at least one sizing portion and at least one treatment portion, and operating the at least one sizing portion of the device to obtain luminal size parameter data. Another exemplary method may further comprise the steps of operating the at least one treatment portion at a location within the vessel lumen at or near a stenotic lesion, whereby operation of the at least one treatment portion is based upon the luminal size parameter data, whereby operation of the at least one treatment portion increases the luminal size parameter data value, and ceasing operation of the at least one treatment portion when the luminal size parameter data indicates a preferred luminal size parameter.

In at least one exemplary device for removing a stenotic lesion of a vessel of the present disclosure, the device comprises at least one sizing portion and at least one treatment portion. In an exemplary embodiment, the treatment portion is operable to remove at least part of a stenotic lesion

BRIEF DESCRIPTION OF THE DRAWINGS

FIG. 3A shows the exemplary sizing device of FIG. 2B, for example, positioned at a second location within the vessel obtaining an additional then-current luminal size parameter, according to the present disclosure;

FIGS. 3B and 3C show cross-sectional views of a vessel having an exemplary sizing device and an exemplary treatment device positioned therein, according to the present disclosure;

FIGS. 6A-6F show various embodiments of exemplary treatment portions of treatment devices, according to the present disclosure;

DETAILED DESCRIPTION

Figure 1A:
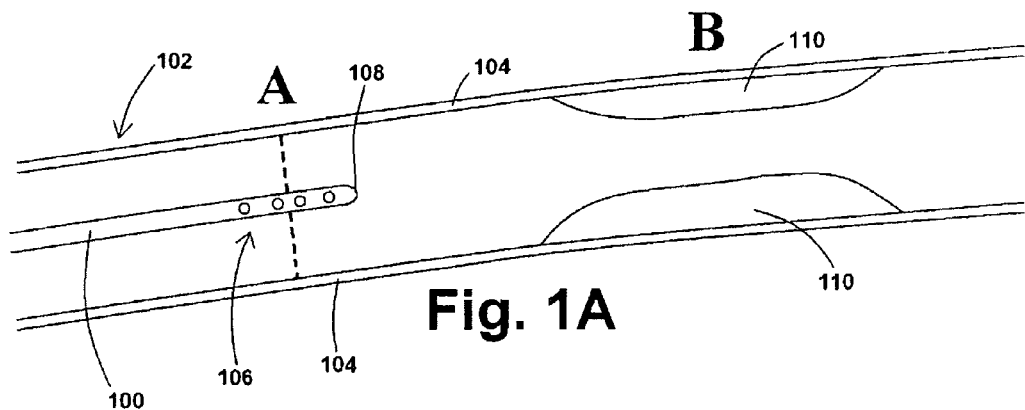
FIG. 1A shows a cross-sectional view of a vessel having a stenotic lesion and an exemplary sizing device positioned therein, according to the present disclosure.

Reference will now be made to the embodiments illustrated in the drawings and specific language will be used to describe the same. It will nevertheless be understood that no limitation of scope is intended by the description of these embodiments.

In at least one embodiment of a method for removing a stenotic lesion of a vessel, the method comprises the steps of measuring at least two luminal parameters, determining a preferred luminal size parameter, and operating a treatment device to increase at least one of the luminal parameters.

In at least one exemplary method for removing a stenotic lesion of a vessel, the method comprises the steps of measuring a first luminal size parameter at a first location within a vessel lumen, measuring a second luminal size parameter at a second location within the vessel lumen, determining a preferred second luminal size parameter based upon the first luminal size parameter and the second luminal size parameter, and positioning a treatment device to at or near the second location. In at least one method, the method further comprises the steps of operating the treatment device to increase the second luminal size parameter and measuring a then-current luminal size parameter at the second location. After the then-current luminal size parameter at the second location is measured, an exemplary method for removing a stenotic lesion of a vessel comprises the step of comparing the then-current luminal size parameter to the preferred second luminal size parameter, and if the then-current luminal size parameter does not equal the preferred second luminal size parameter, an exemplary method comprises repeating the steps of operating the treatment device to increase the second luminal size parameter, measuring another then-current luminal size parameter at the second location, and comparing the then-current luminal size parameter to the preferred second luminal size parameter. In at least one embodiment of such a method, the aforementioned three steps (essentially a feedback loop) are repeated until the then-current luminal size parameter equals the preferred second luminal size parameter.

In various embodiments of methods of the disclosure of the present application, one or more luminal size parameters are measured. In at least one embodiment, the various luminal size parameters (the first luminal size parameter and the second luminal size parameter, for example) comprise luminal diameters. For example, and when performing an exemplary method of the disclosure of the present application to remove a vessel plaque (an exemplary stenotic lesion), a first luminal diameter may be measured at a location within the vessel, and a second luminal diameter may be measured at a second location within the vessel. In another example, the luminal size parameters may comprise luminal cross-sectional areas. In yet another example, the luminal size parameters may comprise one or more other luminal geometric calculations, including, for example, a luminal circumference, each or all of which may share one or more similar calculated components (like a luminal diameter or a luminal radius, for example).

In an exemplary embodiment of a method for removing a stenotic lesion of a vessel of the disclosure of the present application, the first location comprises a location without a stenotic lesion, and the second location comprises a location with a stenotic lesion. Alternatively, and in another exemplary embodiment, the first location comprises a location with a relatively small stenotic lesion, and the second location comprises a location with relatively large stenotic lesion. In either embodiment, or as may be with other embodiments, the luminal size parameters at the first and second locations may vary from one another.

For example, and as shown in FIG. 1A, a sizing device 100 may be positioned within the lumen of a vessel 102 at a first location "A" as shown in the figure. Sizing device 100 may then operate to determine a first luminal size parameter at location "A", for example, as shown in FIG. 1A. As shown in the figure, the first luminal size parameter (as indicated by the dotted line extending from one vessel wall 104 to another) may comprise, for example, a luminal diameter or luminal cross-sectional area. In this exemplary embodiment, sizing device 100 comprises a sizing portion 106 located at or near the distal end 108 of sizing device 100. In such an embodiment, sizing portion 106 of sizing device 100 is the portion of sizing device 100 operable to obtain one or more luminal size parameters. In addition, and as shown in FIG. 1A, sizing portion 106 of sizing device 100 is positioned at a first location within the vessel that does not have a stenotic lesion 110.

Figure 1B:
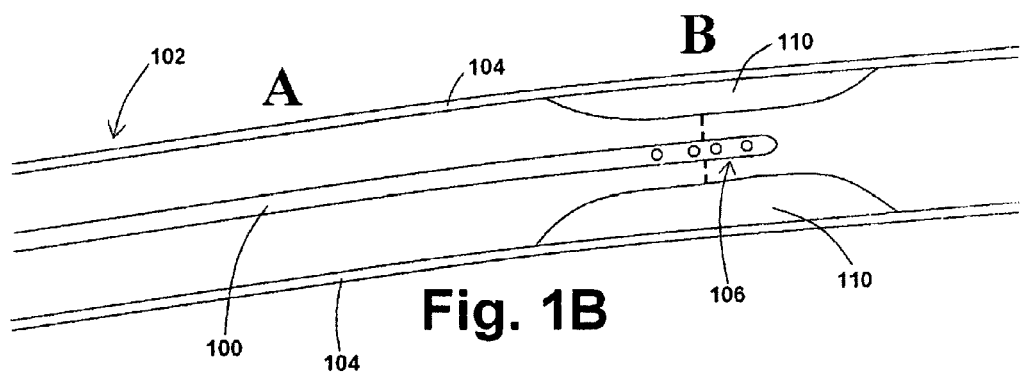
FIG. 1B shows the cross-sectional view of a vessel wherein the exemplary sizing device is positioned at a second location within the vessel, according to the present disclosure.

An exemplary embodiment of a sizing device 100 positioned within the lumen of a vessel 102 at a second location is shown in FIG. 1B. As shown in FIG. 1B, sizing device 100 may be introduced further within vessel 102 to a second location "B" as shown, wherein the second location is a location within vessel 102 having a stenotic lesion 110. In such an embodiment, and as shown in FIG. 1B, sizing device 100 may be operable to determine a second luminal size parameter (as indicated by the dotted line extending from sizing device 100 at second location "B"), noting that, for example, the second luminal size parameter may be relatively smaller than the first luminal size parameter if the second luminal size parameter is obtained at a portion within vessel 102 having a stenotic lesion 110. For example, sizing device 100 may obtain a first luminal diameter at location "A" and a second luminal diameter at location "B", and as shown in FIGS. 1A and 1B, the first luminal diameter would be larger than the second luminal diameter.

Figure 1C:
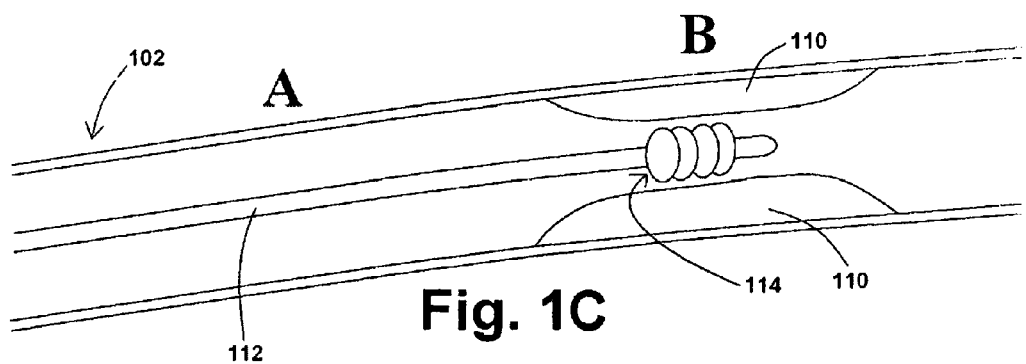
FIG. 1C shows a cross-sectional view of a vessel wherein an exemplary treatment device is positioned at a second location within the vessel, according to the present disclosure.
Figure 2A:
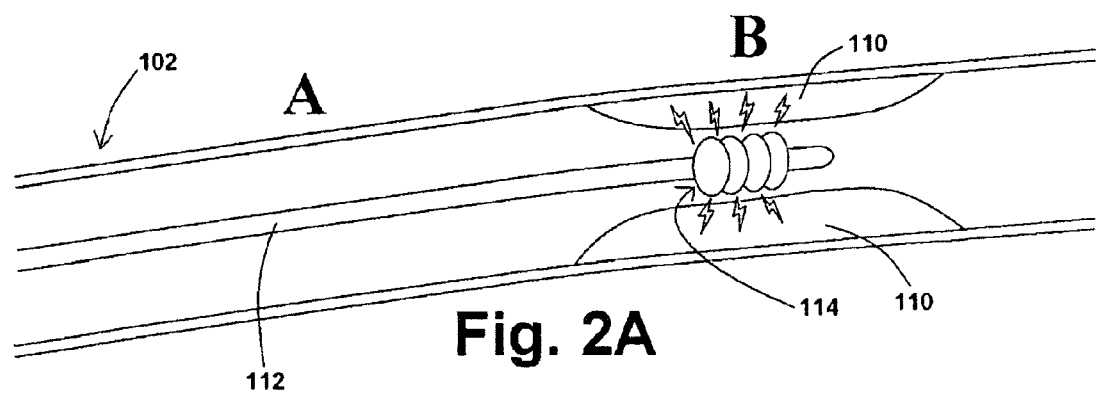
FIG. 2A shows an exemplary treatment device in operation, according to the present disclosure.

An exemplary embodiment of a method for removing a stenotic lesion of a vessel of the present application may comprise the step of positioning a treatment device within a vessel at or near at least one location within the vessel. As shown in FIG. 1C, a treatment device 112 is shown positioned within a lumen of a vessel 102, wherein at least one treatment portion 114 of treatment device 112 is positioned at or near a stenotic lesion 110 present within the lumen of vessel 102. Operation of treatment portion 114 of treatment device 112 is shown in FIG. 2A, with operation of the device indicated by the symbols above and below treatment portion 114. Said operation symbols are not intended to be limited to, for example, the application of electrical current—said symbols are intended merely to visually indicate operation of treatment portion 114 of treatment device 112.

Figure 2B:
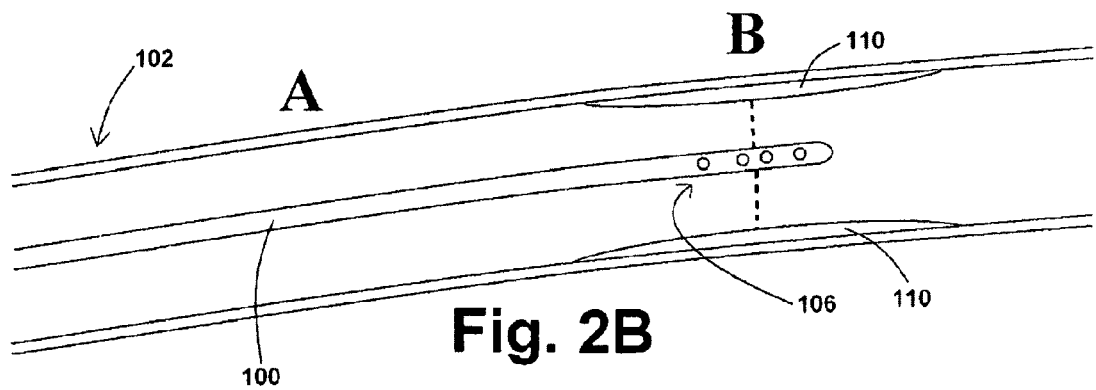
FIG. 2B shows the exemplary sizing device is positioned at a second location within the vessel obtaining a then-current luminal size parameter, according to the present disclosure.

After operation of treatment device 112 as shown in FIG. 2A, a determination as to the potential effectiveness of the treatment may be made by obtaining one or more luminal size parameters at the treatment site. As shown in FIG. 2B, sizing device 100 is present within the lumen of vessel 102, and is operable to obtain a then-current luminal size parameter (as indicated by the dotted line extending from sizing device 100 at second location "B"), which, as shown in the exemplary embodiment depicted in FIG. 2B, is relatively larger than the original second luminal size parameter. In this embodiment, a relatively large then-current luminal size parameter as compared to the original second luminal size parameter is indicative of at least a partially-successful stenotic lesion removal treatment, also as indicated by the smaller stenotic lesions 110 shown in FIG. 2B. A user may compare the then-current luminal size parameter to any number of other obtained luminal size parameters, including, but not limited to, the first luminal size parameter the second luminal size parameter, and a preferred second luminal size parameter, as described within example FIGS. 1A-2B and herein, as appropriate.

For example, and using numerical values merely as an example, if a first luminal size parameter is a vessel diameter of 0.7 mm, and a second luminal size parameter at a location within a vessel 102 having at least one stenotic lesion 110 is 0.2 mm in diameter, a user may select/determine a preferred second luminal size parameter of 0.5 mm in diameter, for example. Such a larger preferred second luminal size parameter relative to the original second luminal size parameter, when achieved based upon a stenotic lesion removal treatment, would be indicative of a partial removal of a stenotic lesion 110 from the vessel 102. A user may instead decide that a preferred second luminal size parameter is equivalent to the first luminal size parameter, which, as described in this particular example, would be indicative of total or near-total removal of a stenotic lesion 110 from a vessel 102 at the treatment site.

Figure 2C:
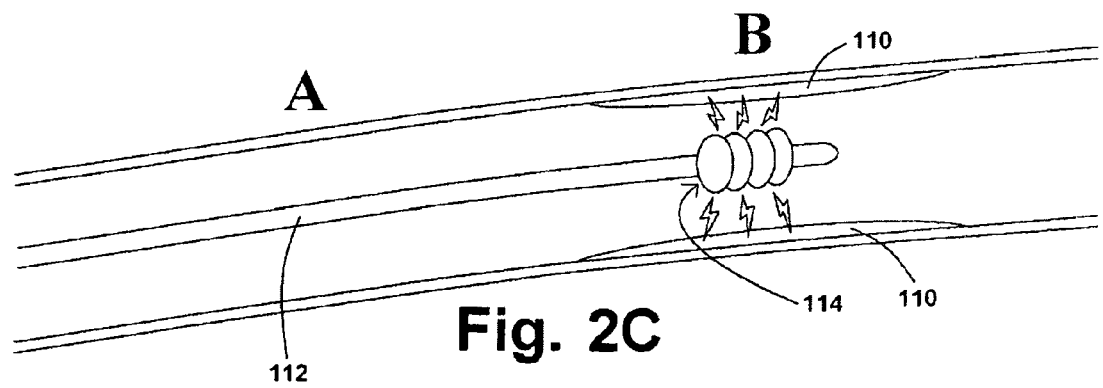
FIG. 2C shows the exemplary treatment device of FIGS. 1C and 2A in operation, according to the present disclosure.

As shown in FIG. 2C, treatment device 112 is shown re-inserted into the treatment site at or near stenotic lesion(s) 110, and is shown operating to potentially remove additional stenotic lesion(s) 110 from the treatment site. The scenario shown in FIG. 2C is indicative of a situation where a user has decided that the previously-measured then-current luminal size parameter is not equal to or within a range of an acceptable/preferred second luminal size parameter, and that the user has decided to continue treatment using treatment device 112 in attempt to remove additional stenotic lesion(s) 110 from the treatment site.

FIG. 3A shows at least a portion of a sizing device present within a vessel after completely successful treatment to remove one or more stenotic lesions. As shown in FIG. 3A, sizing device 100 is positioned within the lumen of vessel 102, whereby sizing portion 106 of sizing device 100 is positioned at or near the original second location (indicated by "B"). Sizing device 100 is shown operating to obtain a then-current luminal size parameter, and in this particular example, and assuming that the vessel has a constant diameter throughout the portion shown in FIG. 3A, the then-current luminal size parameter would equal the original first luminal size parameter, indicative of complete removal of a stenotic lesion at the treatment site. In such a situation, a user may decide to cease treatment (and thus cease operation of treatment device 112) as the then-current luminal size parameter would equal to, or be within, a preferred luminal size parameter, assuming such a preferred luminal size parameter is equal to the original first luminal size parameter.

FIGS. 3B and 3C are indicative of situations where a user is using a sizing device and a treatment device, but does not completely remove one device from a vessel to use the other device. For example, and as shown in FIG. 3B, sizing portion 106 of sizing device 100 is shown positioned at or near stenotic lesion(s) 110, while at least a portion of treatment device 112 remains positioned within the lumen of vessel 102. Similarly, and as shown in FIG. 3C, treatment portion 114 of treatment device 112 is shown positioned at or near stenotic lesion(s) 110, while at least a portion of sizing device 100 remains positioned within the lumen of vessel 102.

Figure 4A:
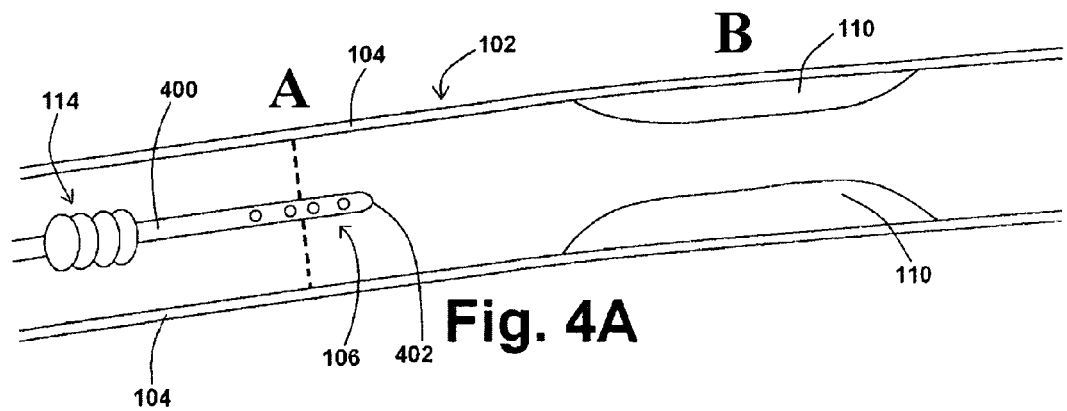
FIG. 4A shows a cross-sectional view of a vessel having a stenotic lesion and an exemplary combination device positioned therein, according to the present disclosure.
Figure 4B:
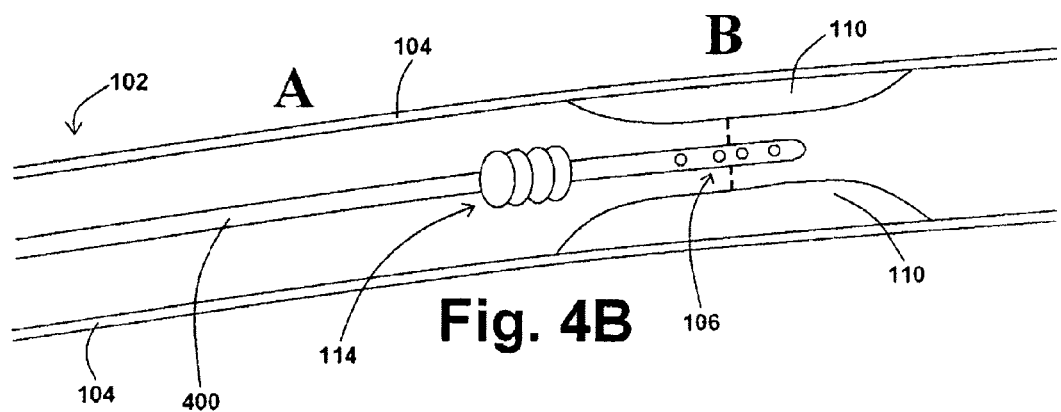
FIGS. 4B, 5A, and 5C show cross-sectional views of a vessel wherein a sizing portion of the exemplary combination device is positioned at a second location within the vessel, according to the present disclosure.
Figure 4C:
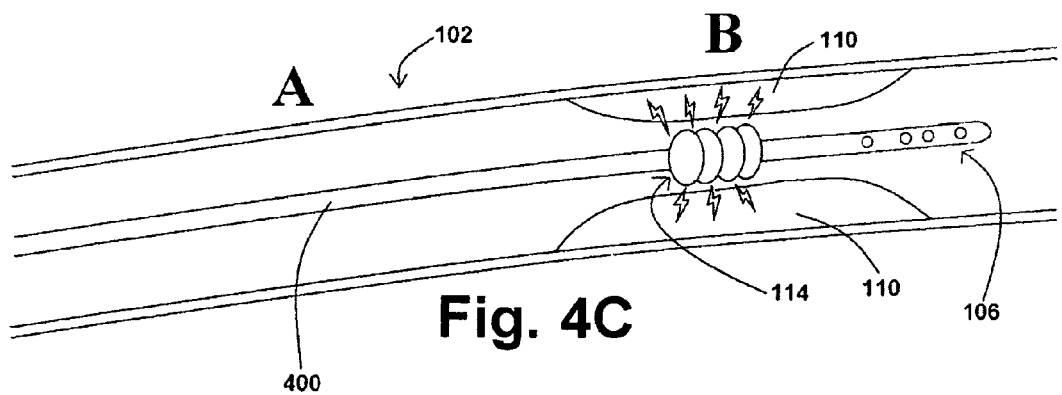
FIGS. 4C and 5B show cross-sectional views of a vessel wherein a treatment portion of the exemplary combination device is positioned at a second location within the vessel and shown in operation, according to the present disclosure.

In at least an additional embodiment of a device of the disclosure of the present application, said device comprises at least one feature indicative of a sizing device and at least one feature indicative of a treatment device. For example, and as shown in FIGS. 4A-4C, an exemplary combination device 400 comprises a sizing portion 106 located at or near the distal end of combination device 400. In addition, and as shown in the exemplary embodiments shown in FIGS. 4A-4C, an exemplary combination device 400 also comprises a treatment portion 114 positioned along combination device. As referenced within the present application, an exemplary combination device 400 may be substantially equivalent, if not completely equivalent, to an exemplary sizing device 100 of the present application comprising at least one treatment portion 114, and similarly, an exemplary combination device 400 may be substantially equivalent, if not completely equivalent, to an exemplary treatment device 112 comprising at least one sizing portion 106.

As shown in FIG. 4A, an exemplary combination device 400 is shown positioned within the lumen of a vessel 102, whereby sizing portion 106 of combination device 400 is positioned at or near a first location within vessel 102 (as indicated by "A"). Combination device 400 may then operate to determine a first luminal size parameter at location "A", for example, as shown in FIG. 4A. As shown in the figure, the first luminal size parameter (as indicated by the dotted line extending from one vessel wall 104 to another) may comprise, for example, a luminal diameter or luminal cross-sectional area. In this exemplary embodiment, combination device 400 comprises a sizing portion 106 located at or near the distal end 402 of sizing device 400. In such an embodiment, sizing portion 106 of combination device 400 is the portion of combination device 400 operable to obtain one or more luminal size parameters. In addition, and as shown in FIG. 4A, sizing portion 106 of combination device 400 is positioned at a first location within the vessel that does not have a stenotic lesion 110.

An exemplary embodiment of a combination device 400 positioned within the lumen of a blood vessel 102 at a second location is shown in FIG. 4B. As shown in FIG. 4B, combination device 400 may be introduced further within vessel 102 to a second location "B" as shown, wherein the second location is a location within vessel 102 having a stenotic lesion 110. In such an embodiment, and as shown in FIG. 4B, combination device 400 may be operable to determine a second luminal size parameter (as indicated by the dotted line extending from combination device 400 at second location "B"), noting that, for example, the second luminal size parameter may be relatively smaller than the first luminal size parameter if the second luminal size parameter is obtained at a portion within vessel 102 having a stenotic lesion 110. For example, combination device 400 may obtain a first luminal diameter at location "A" and a second luminal diameter at location "B", and the first luminal diameter would be larger than the second luminal diameter.

An exemplary embodiment of a method for removing a stenotic lesion of a vessel of the present application may comprise the step of positioning a combination/treatment device within a vessel at or near at least one location within the vessel. As shown in FIG. 4C, combination device 400 is shown positioned within a lumen of a vessel 102, wherein at least one treatment portion 114 of combination device 400 is positioned at or near a stenotic lesion 110 present within the lumen of vessel 102. Operation of treatment portion 114 of combination device 400 is also shown in FIG. 4C, with operation of the device indicated by the symbols above and below treatment portion 114. As referenced above in connection with the operation of an exemplary treatment device 112, said operation symbols are not intended to be limited to, for example, the application of electrical current—said symbols are intended merely to visually indicate operation of treatment portion 114 of combination device 400.

Figure 5A:
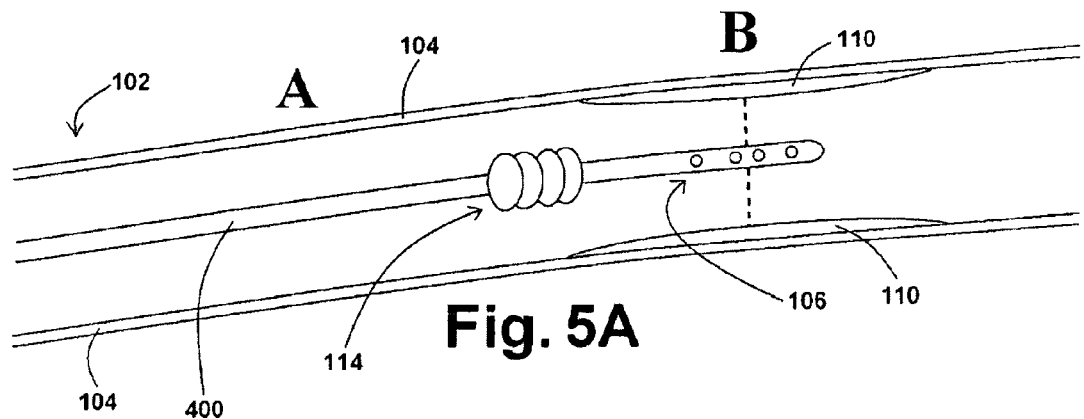

As shown in FIG. 5A, combination device 400 is re-positioned within the lumen of vessel 102, and is operable to obtain a then-current luminal size parameter (as indicated by the dotted line extending from combination device 400 at second location "B"), which, as shown in the exemplary embodiment depicted in FIG. 5A, is relatively larger than the original second luminal size parameter. In this embodiment, a relatively large then-current luminal size parameter as compared to the original second luminal size parameter is indicative of at least a partially-successful treatment, also as indicated by the smaller stenotic lesions 110 shown in FIG. 5A. A user may compare the then-current luminal size parameter to any number of other obtained luminal size parameters, including, but not limited to, the first luminal size parameter the second luminal size parameter, and a preferred second luminal size parameter, as described within example FIGS. 4A-5A and herein, as appropriate.

Figure 5B:
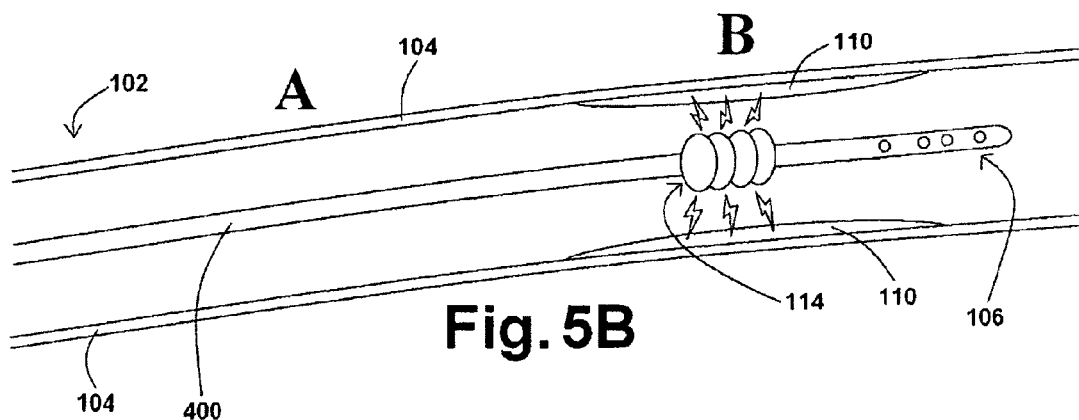

As shown in FIG. 5B, combination device 400 is shown re-positioned within vessel 102 so that treatment portion 114 is positioned at or near stenotic lesion(s) 110, and is shown operating to potentially remove additional stenotic lesion(s) 110 from the treatment site. The scenario shown in FIG. 5B is indicative of a situation where a user has decided that the previously-measured then-current luminal size parameter is not equal to or within a range of an acceptable/preferred second luminal size parameter, and that the user has decided to continue treatment using treatment portion 114 of combination device 400 in attempt to remove additional stenotic lesion(s) 110 from the treatment site.

Figure 5C:
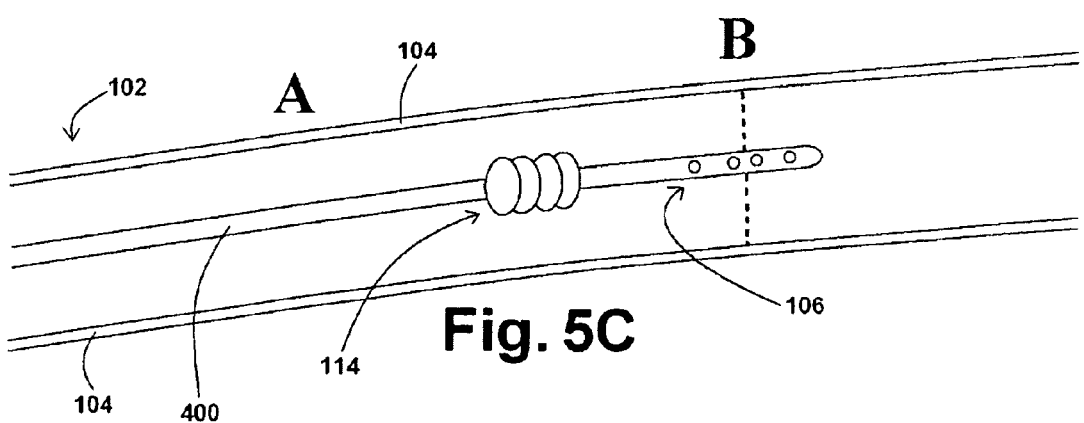

FIG. 5C shows at least a portion of a combination device 400 present within a vessel after completely successful treatment to remove one or more stenotic lesions. As shown in FIG. 5C, combination device 400 is re-positioned within the lumen of vessel 102, whereby sizing portion 106 of combination device 400 is positioned at or near the original second location (indicated by "B"). Combination device 400 is shown operating to obtain a then-current luminal size parameter, and in this particular example, and assuming that the vessel has a constant diameter throughout the portion shown in FIG. 5C, the then-current luminal size parameter would equal the original first luminal size parameter, indicative of complete removal of a stenotic lesion at the treatment site. In such a situation, a user may decide to cease treatment (and thus cease operation of treatment device 112) as the then-current luminal size parameter would equal to, or be within, a preferred luminal size parameter, assuming such a preferred luminal size parameter is equal to the original first luminal size parameter.

In at least one embodiment of a treatment portion 114 of the present application, treatment portion 114 comprises a treatment portion selected from the group consisting of a cutting balloon, a cryoplasty device, a rotational atherectomy device, a laser angioplasty device, a vibrating catheter, and a vibrating drill. A common feature shared among these various treatment portion 114 compositions is that each one is operable to remove at least a portion of a stenotic lesion 110 from a vessel or luminal organ. As such, a number of other treatment portion 114 compositions either known or developed in the art may be useful in connection with the present disclosure so long as it is operable to remove at least a portion of a stenotic lesion 110 from a vessel or luminal organ. As referenced herein, the term "vessel" is intended to encompass any number of luminal organs, including blood vessels, present within a body.

FIGS. 6A-6F show various embodiments of at least part of various treatment portions 114 of exemplary treatment devices 112 of the present disclosure. FIG. 6A shows an exemplary treatment device 112 of the present disclosure positioned within a vessel 102, wherein said treatment device 112 comprises a treatment portion 114 comprising a cutting balloon 600. Cutting balloon 600, as shown in FIG. 6A, may comprise one or more cutting portions 602, wherein said cutting portions are operable to physically cut a stenotic lesion 110 positioned within a vessel 102. In at least one embodiment, cutting balloon 600 may be inflated within the lumen of a vessel 102, whereby the inflation of cutting balloon 600 allows cutting portions 602 to engage and cut a stenotic lesion 110.

Another embodiment of a treatment portion 114 of a treatment device 112 of the present disclosure is shown in FIG. 6B. As shown in FIG. 6B, treatment portion 114 comprises a cryo-balloon 604 (an exemplary cryoplasty device) capable of inflation using a relatively cold gas and/or fluid such as nitrous oxide. Inflation of cryo-balloon 604 using a cold gas and/or fluid locally reduces the temperature within a vessel 102, providing potential benefits of being able to crack and/or remove a stenotic lesion 110 within said vessel 602.

An additional embodiment of an exemplary treatment device 112 of the present application is shown in FIG. 6C. As shown in FIG. 6C, treatment device 112 comprises a rotational atherectomy device 606, whereby rotation of rotational atherectomy device 606 operates to cut a stenotic lesion 110 positioned within a vessel 102. An exemplary rotational atherectomy device 606 comprises at least one component capable of cutting a stenotic lesion 110.

FIG. 6D shows an embodiment of a treatment portion 114 of a treatment device 112 comprising a laser angioplasty device 608. As shown in FIG. 6D, laser angioplasty device 608 may be positioned at the distal end of treatment device 112, and is operable to emit beams of light (lasers) capable of disintegrating some or all of a stenotic lesion 110.

Additional embodiments of treatment portions 114 of exemplary treatment devices 112 of the disclosure of the present application are shown in FIGS. 6E and 6F. As shown in FIG. 6E, treatment portion 114 comprises a vibrating catheter 610 capable of vibration, for example, in the directions shown by the arrow in the figure. Vibrating catheter 610, when in operation, may physically remove some or all of a stenotic lesion 110 impacted by vibrating catheter 610. As shown in FIG. 6E, treatment portion 114 may comprise a vibrating drill 612, whereby vibrating drill 612 may operate similarly to vibrating catheter 610 as described above, and may be further operable to drill through a stenotic lesion 110 using drill tip 614.

The exemplary embodiments of treatment devices 114 shown in FIGS. 6A-6F and described herein are not intended to be an exhaustive list and/or description of treatment devices 112 of the present application, as one or more additional treatment devices 114 known in the art may be useful in one or more devices, systems, and/or methods of the present application.

Figure 7A:
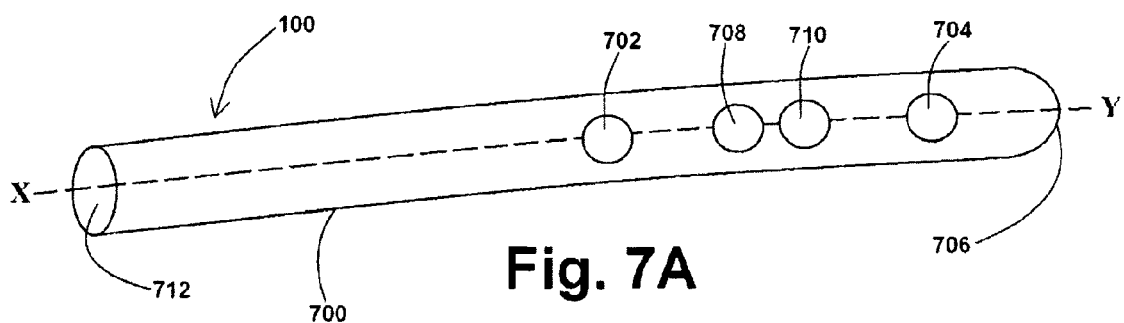
FIGS. 7A, 7B, and 7C show at least a portion of exemplary embodiments of sizing devices, according to the present disclosure.

As shown in FIGS. 1A and 1B, for example, a sizing device 100 is used to determine the various luminal size parameters. In at least one embodiment of at least a portion of sizing device 100, and as shown in FIG. 7A, sizing device 100 may comprise an elongated body 700 having a longitudinal axis extending from a proximal end to a distal end (as indicated by the dotted line extending from "X" to "Y" as shown in FIG. 5A). An exemplary sizing device 100 of the present disclosure may also comprise a first excitation electrode 702 and a second excitation electrode 704 positioned along the longitudinal axis of the elongated body 700 at or near a distal end 706 of the elongated body 700, and may further comprise a first detection electrode 708 and a second detection electrode 710 positioned along the longitudinal axis of the elongated body 700 in between the first excitation electrode 702 and the second excitation electrode 704. In at least one exemplary embodiment of a sizing device 100, the elongated body 700 comprises a catheter having a lumen extending along the longitudinal axis of the catheter. Furthermore, other sizing portions 106 not specifically disclosed herein but insertable within a vessel and operable to determine at least one luminal size parameter may comprise and/or be used within an exemplary device, system, and/or method of the present disclosure.

In at least one embodiment, operation of sizing device 100, sizing portion 106 of sizing device 100, or a sizing portion 106 of another device and/or system of the present disclosure, including technical operation of one or more electrodes disclosed herein to determine one or more luminal size parameters, is performed as disclosed within one or more of the patents and/or patent applications incorporated by reference herein, including, but not limited to, the disclosure of U.S. Pat. No. 7,454,244. For example, and with reference to an exemplary embodiment of a sizing portion 106 disclosed herein comprising electrodes as referenced herein, conductance of current flow through an organ lumen and organ wall and surrounding tissue is parallel; i.e., $$G(z, t) = \frac{CSA(z, t) \cdot C_b}{L} + G_p(z, t) \quad [1a]$$

where $G_p(z,t)$ is the effective conductance of the structure outside the bodily fluid (organ wall and surrounding tissue) at a given position, z, along the long axis of the organ at a given time, t, and $C_b$ is the electrical conductivity of the bodily fluid which for blood generally depends on the temperature, hematocrit and orientation and deformation of blood cells, and L is the distance between the detection electrodes of sizing portion 106. Furthermore, Equation [1a] can be rearranged to solve for an exemplary luminal size parameter, namely cross sectional area CSA(t), with a correction factor, a, if the electric field is non-homogeneous, as $$CSA(z, t) = \frac{L}{\alpha C_b}[G(z, t) - G_p(z, t)] \quad [1b]$$

where α would be equal to 1 if the field were completely homogeneous. The parallel conductance, $G_p$, is an offset error that results from current leakage.

Figure 7B:
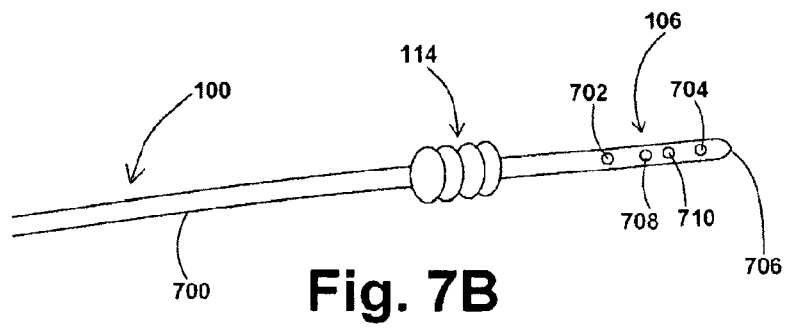
Figure 7C:
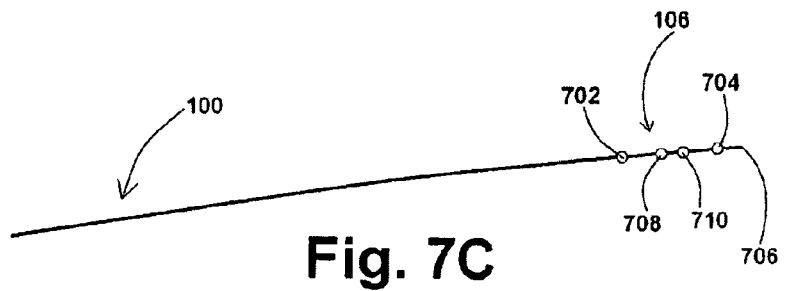

FIG. 7B shows an exemplary embodiment of a sizing device 100 comprising both a treatment portion 114 and a sizing portion 106. As shown in this exemplary embodiment, sizing portion 106 of device 100 comprises a first excitation electrode 702 and a second excitation electrode 704 positioned along elongated body 700 at or near a distal end 706 of the elongated body 700, and further comprises a first detection electrode 708 and a second detection electrode 710 positioned along the elongated body 700 in between the first excitation electrode 702 and the second excitation electrode 704. In this exemplary embodiment, sizing device 100, comprising both a treatment portion 114 and a sizing portion 106, may be substantially equivalent, if not completely equivalent, to an exemplary combination device 400 of the present application An additional exemplary embodiment of a sizing device 100 of the disclosure of the present application is shown in FIG. 7C. As shown in FIG. 7C, sizing device 100 comprises a wire having a first excitation electrode 702, a second excitation electrode 704, a first detection electrode 708, and a second detection electrode 710 positioned along the wire at or near the distal end 706 of sizing device 100.

Exemplary sizing devices 100 of the disclosure of the present application, as referenced herein, are operable to measure various luminal size parameters. In at least one embodiment wherein the elongated body of the sizing device 100 or treatment device 112 comprises a catheter having a lumen extending along the longitudinal axis of the catheter, an exemplary method for removing a stenotic lesion of a vessel of the present application comprises the step of measuring a first luminal size parameter which comprises the steps of providing electrical current flow to the first location through the catheter, injecting a first solution of a first compound having a first conductivity into the vessel lumen at the first location through the catheter, and measuring a first conductance value at the first location. An exemplary method may further comprise the steps of injecting a second solution of a second compound having a second conductivity into the vessel lumen at the first location through the catheter, measuring a second conductance value at the first location, and calculating a first luminal size parameter based on the first conductance value, the second conductance value, the first conductivity of the first solution, and the second conductivity of the second solution. Such a method could be used to measure a second and/or subsequent luminal size parameter, noting that the location of the measuring of the conductance values may vary accordingly (for example, at a second location).

For example, and as referenced within priority U.S. Pat. No. 7,454,244 incorporated by reference in its entirety herein, at any given position, z, along the long axis of organ/vessel and at any given time, t, in the cardiac cycle, $G_p$ is a constant. Hence, two injections of different concentrations and/or conductivities of an NaCl solution give rise to two equations:

$$C_1 \cdot CSA(z,t) + L \cdot G_p(z,t) = L \cdot G_1(z,t) \quad [2]$$

and $$C_2 \cdot CSA(z,t) + L \cdot G_p(z,t) = L \cdot G_2(z,t) \quad [3]$$

which can be solved simultaneously for CSA and $G_p$ as $$CSA(z,t) = L \frac{[G_2(z,t) - G_1(z,t)]}{[C_2 - C_1]} \quad [4]$$

And $$G_p(z,t) = \frac{[C_2 \cdot G_1(z,t) - C_1 \cdot G_2(z,t)]}{[C_2 - C_1]} \quad [5]$$

where subscript "1" and subscript "2" designate any two injections of different NaCl concentrations and/or conductivities. For each injection k, $C_k$ gives rise to $G_k$ which is measured as the ratio of the root mean square of the current divided by the root mean square of the voltage. The $C_k$ is typically determined through in vitro calibration for the various NaCl concentrations and/or conductivities. The concentration of NaCl used is typically on the order of 0.45 to 1.8%. The volume of NaCl solution is typically about 5 ml, but sufficient to displace the entire local vascular blood volume momentarily. The values of CSA(t) and $G_p$(t) can be determined at end-diastole or end-systole (i.e., the minimum and maximum values) or the mean thereof.

In an exemplary embodiment of method for removing a stenotic lesion of a vessel of the present application, a sizing device 100 useful to measure the various luminal size parameters comprises a wire (as shown in FIG. 7C), and the treatment device 112 operable to increase at least one luminal size parameter comprises a catheter comprising at least one treatment portion 114. In at least one embodiment, the wire comprises a first excitation electrode 702 and a second excitation electrode 704 positioned along sizing device 100, and further comprises a first detection electrode 708 and a second detection electrode 710 positioned along sizing device 100 in between the first excitation electrode 702 and the second excitation electrode 706.

In another exemplary embodiment of a sizing device 100, sizing device 100 may comprise a guide wire, wherein such a guide wire may be positioned at least partially within a lumen of the catheter to guide the catheter within a vessel and to perform at least one method step of an exemplary method of the present disclosure.

In an exemplary embodiment of a treatment device 112 of the disclosure of the present application, treatment device 112 comprises at least one treatment portion 114 and at least one sizing portion 106. In at least one embodiment, the treatment portion 114 of treatment device 112 is operable to remove at least part of a stenotic lesion. In various embodiments, an exemplary treatment portion 114 of treatment device 112 (or a sizing device 100 or a combination device 400) may comprises a cutting balloon, a cryoplasty device, a rotational atherectomy device, a laser angioplasty device, a vibrating catheter, and a vibrating drill, exemplary embodiments of each of the same as shown in FIGS. 6A-6F and described herein.

In at least one embodiment of an exemplary sizing portion 106 of one or more devices of the present disclosure, sizing portion 106 comprises a first excitation electrode 702 and a second excitation electrode 704 positioned along the device, and further comprises a first detection electrode 708 and a second detection electrode 710 positioned along the device in between the first excitation electrode 702 and the second excitation electrode 704. In another embodiment wherein an exemplary treatment portion 114 comprises a balloon 800 (as shown, for example, in FIG. 8A, discussed below), the sizing portion 106 of an exemplary device of the disclosure of the present application may comprises the same or similar configuration of electrodes. For example, and in at least one embodiment, first excitation electrode 702, second excitation electrode 704, first detection electrode 708, and second detection electrode 710 may each be positioned along a treatment device 112 within balloon 800, and wherein the then-current luminal size parameter comprises a parameter measured within balloon 800 at one or more stages of balloon 800 inflation.

Figure 8A:
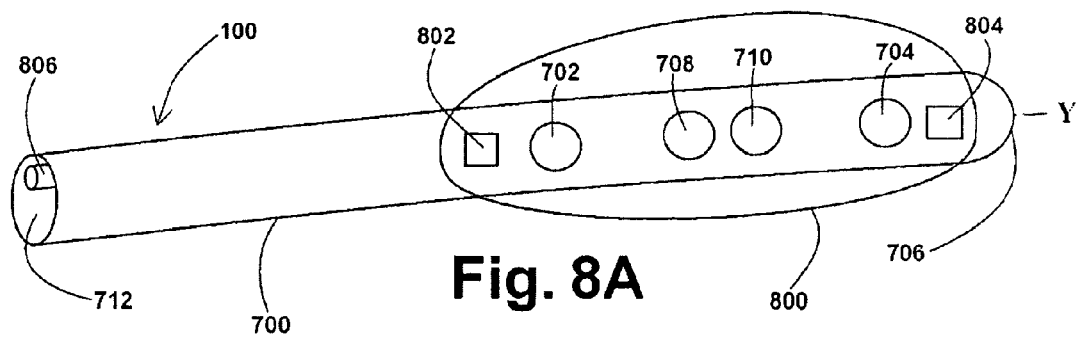
FIG. 8A shows an exemplary embodiment of a sizing device comprising a balloon coupled thereto, according to the present disclosure.

In at least an additional embodiment of an exemplary device of the present application, the device comprises an exemplary treatment portion 114 comprising a balloon 800, and further comprises an exemplary sizing portion 106 comprising at least one pressure sensor 802. As shown in FIG. 8A, an exemplary sizing device 100 comprises balloon 800 surrounding the various electrodes positioned along the elongated body 700 of sizing device 100. In an exemplary embodiment, pressure sensor 802 is operable to detect at least one pressure within balloon 800 at one or more stages of balloon 800 inflation. As shown in FIG. 8A, balloon 800 may inflate and/or deflate via inflation/deflation port 804, allowing a gas and/or a liquid to be introduced into or removed from balloon 800 via suction/infusion tube 806.

As described herein, a user of one or more devices comprising at least one treatment portion 114 may, at some point, decide to stop operating treatment portion 114. The decision to stop may be for any number of reasons, including, but not limited to, achieving a preferred luminal size parameter based upon operation of treatment portion 114 on a stenotic lesion 110 within a vessel. In at least one embodiment of an exemplary method for removing a stenotic lesion of a vessel of the present disclosure, the method further comprises the step of ceasing operation of the treatment device 112 (or the treatment portion 114 of a device of the disclosure of the present application) when the then-current luminal size parameter equals the preferred second luminal size parameter. In at least one embodiment, the preferred second luminal size parameter is equal to the first luminal size parameter. In another embodiment, the preferred luminal size parameter comprises a preferred second luminal size parameter range.

In an exemplary embodiment of a method for removing a stenotic lesion of the present disclosure, the step of comparing the then-current luminal size parameter to the preferred second luminal size parameter comprises comparing the then-current luminal size parameter to the preferred second luminal size parameter range. In such a situation, and instead of a specific numerical size parameter target, the preferred luminal size parameter comprises a range of acceptable values. In an exemplary embodiment, a method for removing a stenotic lesion may comprise the step of ceasing the operation of treatment device 112 (or the treatment portion 114 of a device of the disclosure of the present application) when the then-current luminal size parameter is within the preferred second luminal size parameter range.

Figure 8B:
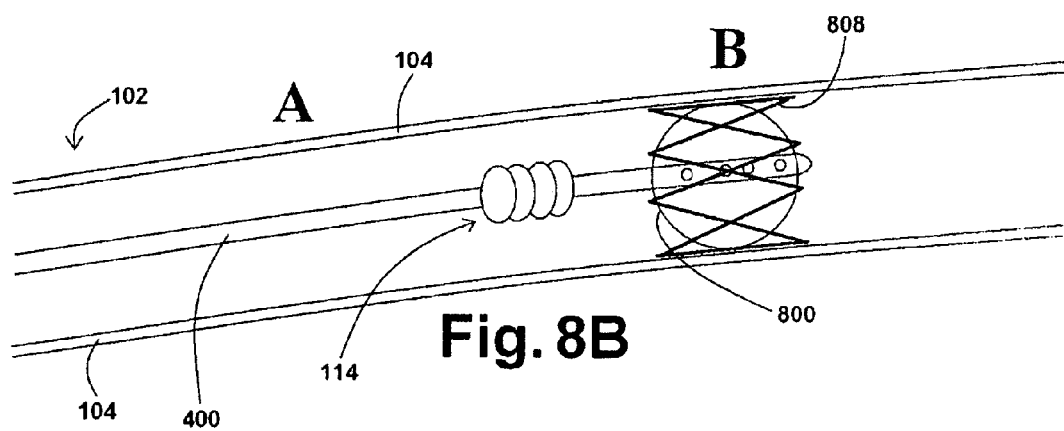
FIGS. 8B and 8C show exemplary embodiments placing stents within a vessel, according to the present disclosure.
Figure 8C:
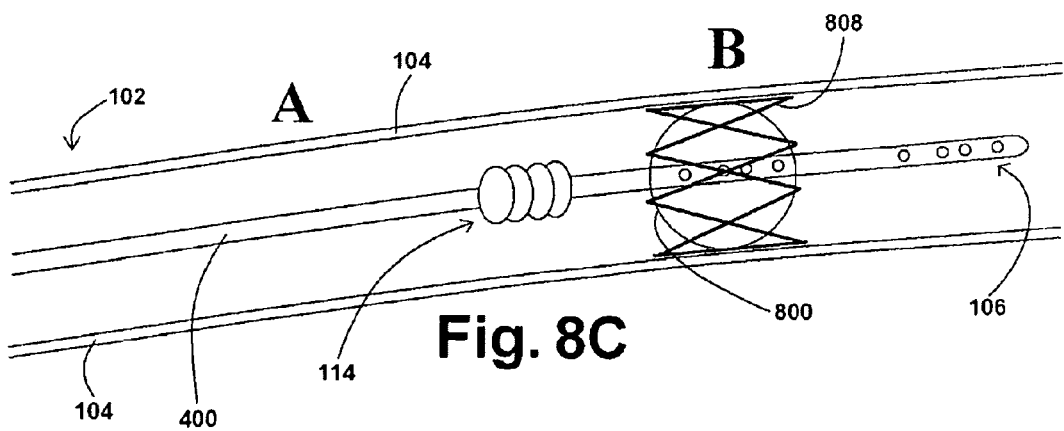

In at least one method for removing a stenotic lesion of the disclosure of the present application, the method further comprises the steps of selecting an appropriately-sized stent and implanting the stent into the vessel lumen. As shown in FIG. 8B, an exemplary device of the present application (shown as combination device 400) comprises a balloon 800 coupled thereto, and is shown in an inflated state while positioning a stent 808 within the lumen of a vessel 102. In another embodiment, and as shown in FIG. 8C, combination device 400 is shown performing a similar operation, noting that in this exemplary embodiment, combination device comprises a treatment portion 114, a sizing portion 106, and a balloon 800 positioned around various electrodes.

In at least one method for removing a stenotic lesion of the disclosure of the present application, the method further comprises the steps of obtaining at least one additional luminal size parameter between the first position and the second position, and constructing a lumen profile based upon the second luminal size parameter and the at least one additional luminal size parameter. In such a situation, multiple luminal size parameters may be used to construct a visual profile of changes in luminal size parameter over time and/or during treatment. In an exemplary method, multiple luminal size parameters are taken at various locations, allowing for the determination of a length of a stenotic lesion to be made based upon the lumen profile.

Figure 9A:
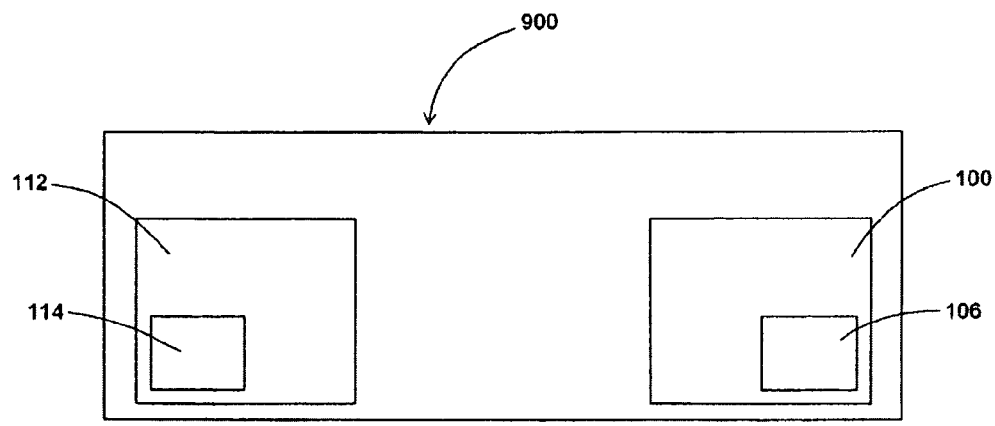
FIGS. 9A and 9B show exemplary embodiments of systems useful for removing stenotic lesions from vessels, according to the present disclosure.

In at least one embodiment of a system for removing a stenotic lesion of a vessel as shown in FIG. 9A, system 900 comprises a treatment device 112 and a sizing device 100. As referenced herein, and as shown in FIG. 9A, treatment device 112 may comprise at least one treatment portion 114 operable to remove at least part of a stenotic lesion 110, and an exemplary sizing device 100 may comprise at least one sizing portion 106 (including various electrodes, for example) operable to measure a first luminal size parameter when sizing device 100 is positioned at a first location, and further operable to measure a second luminal size parameter when sizing device 100 is positioned at a second location.

Any or all of the characteristics, features, elements, and/or limitations of the various devices referenced herein in connection with the above-referenced methods may apply to one or more exemplary systems of the present application. For example, and in an exemplary system 900, treatment device 112 may comprise a catheter, and sizing device 100 may comprises a wire selected from the group consisting of a guide wire, a pressure wire, and a flow wire. Said wire, when in use, may be positioned at least partially within a lumen of the catheter.

Figure 9B:
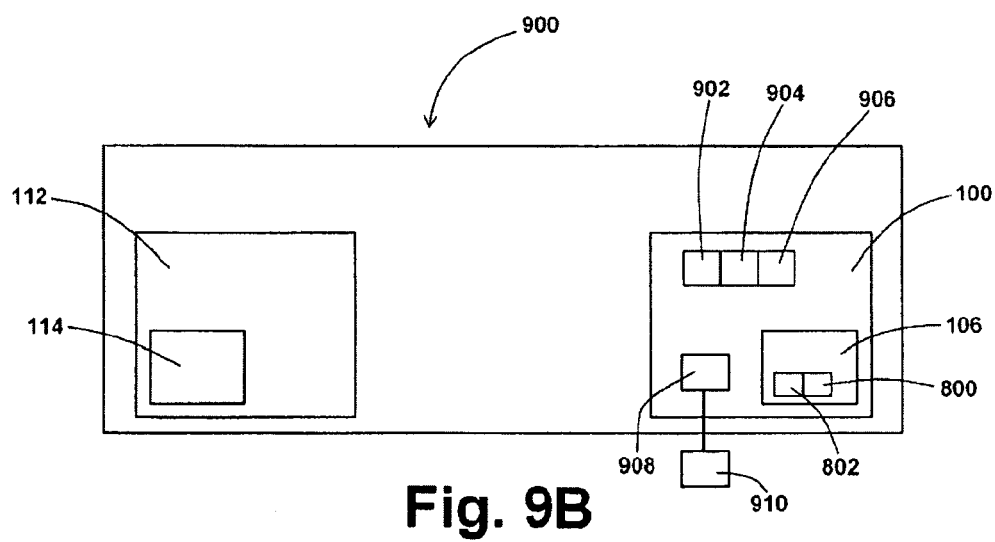

As shown in FIG. 9B, and in at least one embodiment of a system 900 for removing a stenotic lesion of a vessel of the present disclosure, treatment portion 114 of treatment device 112 comprises balloon 800, and sizing portion 106 of sizing device 100 comprises at least one pressure sensor 802. In such an embodiment, pressure sensor 802 may be operable to detect at least one pressure within balloon 800 at one or more stages of balloon inflation. In addition, and in an exemplary embodiment, pressure sensor 802 may be operable to measure a first pressure gradient and calculate at least one luminal parameter within balloon 800 based in part upon the first pressure gradient.

In at least one embodiment of a system for removing a stenotic lesion of a vessel, and as shown in FIG. 9B, system 900 further comprises at least one suction/infusion port 902 in communication with at least one lumen 904 of sizing device 100, said suction/infusion port 902 operable to facilitate one or more fluid injections into a treatment site. In another embodiment, and as shown in FIG. 9B, system 900 may further comprise at least one fluid delivery source 906 operably coupled to lumen 904 of sizing device 100, whereby one or more fluids may be injected from fluid delivery source 906 through lumen 904 of sizing device 100, through suction/infusion port 902, and into the treatment site.

In an additional exemplary embodiment, system 900 may further comprise a data acquisition and processing system 908 operably coupled to sizing device 100 as shown in FIG. 9B, whereby data acquisition and processing system 908 is operable to receive conductance data from sizing device 100. In at least one embodiment, data acquisition and processing system 908 is further operable to calculate at least one luminal parameter based upon said conductance data. In at least another embodiment, data acquisition and processing system 908 is further operable to display the calculated at least one luminal parameter to facilitate operational control of treatment device 112. Said parameter, along with potentially other data and/or parameters, may be displayed on, for example, a display 910 operably coupled to data acquisition and processing system 908 as shown in FIG. 9B.

Figure 9C:
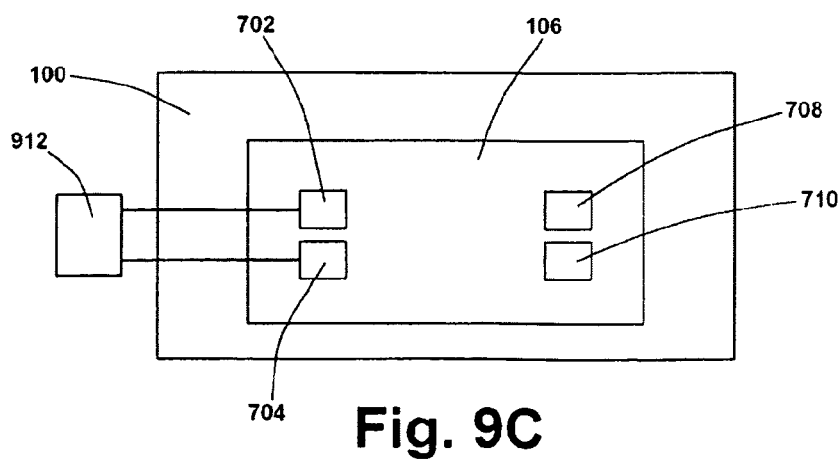
FIG. 9C shows an exemplary embodiment of a sizing device, according to the present disclosure.

In at least one embodiment of a system for removing a stenotic lesion of a vessel, and as shown in FIG. 9C, an exemplary sizing device 100 comprises at least one sizing portion 106. Sizing portion 106, as shown in the embodiment of sizing device 100 in FIG. 9C, may comprise a first excitation electrode 702, a second excitation electrode 704, a first detection electrode 708, and a second detection electrode 710, and may further comprise a current source 912 in communication with first excitation electrode 702 and second excitation electrode 704. In at least one embodiment, current source 912 is operable to supply current to first excitation electrode 702 and second excitation electrode 704 to facilitate measurement of at least one conductance value, thereby facilitating calculation of a luminal size parameter.

In at least one method for removing a stenotic lesion of a vessel of the disclosure of the present application, the method comprises the steps of positioning a device within a vessel lumen, the device (for example, a combination device 400 as shown in FIGS. 4A-5C) comprising at least one sizing portion 106 and at least one treatment portion 114, and operating sizing portion 106 of combination device 400 to obtain luminal size parameter data. An exemplary method may further comprise the steps of operating treatment portion 114 at a location within the vessel lumen at or near a stenotic lesion 110, whereby operation of treatment portion 114 is based upon the luminal size parameter data, and whereby operation of treatment portion 114 increases the luminal size parameter data value. Such a method may further comprise the step of ceasing operation of treatment portion 114 of combination device 400 when the luminal size parameter data indicates a preferred luminal size parameter.

In at least one embodiment of a method for removing a stenotic lesion of a vessel of the disclosure of the present application, the luminal size parameter data is displayed on a display 910 (such as a computer monitor, other monitor, or LCD display, for example), and the step of operating treatment portion 114 is performed based upon the displayed luminal size parameter data. In an exemplary embodiment, the luminal size perimeter data comprises a first luminal size parameter obtained at a first location within the vessel lumen, a second luminal size parameter obtained at a second location within the vessel lumen, and at least one then-current luminal size parameter obtained after initial operation of the at least one treatment portion. Said parameters may be as previously described herein regarding one or more methods of the present disclosure, and may comprise, for example, diameters and/or cross-sectional areas. In at least one embodiment of such a method, the preferred luminal size parameter is determined based upon luminal size parameter data obtained at a location within the vessel lumen without a stenotic lesion 110. In another embodiment, the preferred luminal size parameter is larger than luminal size parameter data obtained at a location within the vessel lumen at or near a stenotic lesion.

In at least one embodiment of a sizing portion 106 of a combination device 400 operable to facilitate performance of one or more methods of the present disclosure, sizing portion 106 comprises a first excitation electrode 702 and a second excitation electrode 704 positioned along combination device 400 at or near a distal end 706 of combination device 400, and further comprises a first detection electrode 708 and a second detection electrode 710 positioned along combination device 400 in between first excitation electrode 702 and second excitation electrode 704. Such an embodiment may comprise an embodiment of a device similar to or the same as the embodiment of an exemplary sizing device 100 as shown in FIG. 7B. In addition, said combination device 400 may comprise one or more features, elements, and/or limitations of one or more other devices and/or systems (or portions thereof) referenced herein, including, but not limited to, an exemplary sizing device 100, an exemplary treatment device 112, and/or an exemplary system 900.

In addition to the foregoing, and in at least one embodiment of a method for removing a stenotic lesion of a vessel of the disclosure of the present application, the step of operating the at least one sizing portion 106 may comprise obtaining multiple luminal size parameter values during the step of operating the at least one treatment portion 114.

In at least one embodiment of a device for removing a stenotic lesion of a vessel of the disclosure of the present application, the device (for example, a combination device 400) comprises at least one sizing portion 106 and at least one treatment portion 114. Sizing portion 106 and/or treatment portion 114 may comprise one or more features, elements, and/or limitations of one or more other devices and/or systems (or portions thereof) referenced herein, including, but not limited to, an exemplary sizing device 100, an exemplary treatment device 112, and/or an exemplary system 900.

While various embodiments of devices, systems, and methods for removing stenotic lesions of vessels have been described in considerable detail herein, the embodiments are merely offered by way of non-limiting examples of the disclosure described herein. Many variations and modifications of the embodiments described herein will be apparent to one of ordinary skill in the art in light of this disclosure. It will therefore be understood by those skilled in the art that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations of the present disclosure. In addition, disclosure directed to a method and/or process should not be limited to the performance of their steps in the order written, and one skilled in the art can readily appreciate that the sequences may be varied and still remain within the spirit and scope of the present disclosure.

It is therefore intended that the disclosure will include all modifications and changes apparent to those of ordinary skill in the art based on this disclosure.

The invention claimed is:

1. A method of removing a stenotic lesion from a vessel, comprising the steps of:
   (a) measuring a first luminal size parameter at a first location within a vessel and a second luminal size parameter at a second location within the vessel;
   (b) determining a preferred luminal size parameter range based upon the first luminal size parameter and the second luminal size parameter;
   (c) operating a treatment device positioned at the second location to increase the second luminal size parameter, the treatment device comprising at least one sizing portion configured to obtain the first luminal size parameter and the second luminal size parameter using impedance and at least one treatment portion operable to remove at least part of a stenotic lesion;
   (d) measuring a then-current luminal size parameter at the second location;
   (e) comparing the then-current luminal size parameter to the preferred luminal size parameter range; and
   (f) if the then-current luminal size parameter does not fall within the preferred luminal size parameter range, repeating steps (c), (d), and (e) until the then-current luminal size parameter falls within the preferred luminal size parameter range.

2. The method of claim 1, wherein the first luminal size parameter is selected from the group consisting of a first luminal diameter and a first luminal cross-sectional area, and wherein the second luminal size parameter is selected from the group consisting of a second luminal diameter and a second luminal cross-sectional area.

3. The method of claim 1, wherein the first location comprises a location without the stenotic lesion, and wherein the second location comprises a location with the stenotic lesion.

4. The method of claim 1, wherein the first location comprises a location with a relatively small stenotic lesion, and wherein the second location comprises a location with relatively large stenotic lesion.

5. The method of claim 1, further comprising the step of:
   ceasing the operation of the treatment device when the then-current second luminal size parameter falls within the preferred luminal size parameter range.

6. The method of claim 1, further comprising the steps of:
   selecting an appropriately-sized stent based in part upon the then-current luminal size parameter; and
   implanting the stent into the vessel lumen.

7. The method of claim 1, further comprising the steps of:
   obtaining at least one additional luminal size parameter between the first location and the second location; and
   constructing a lumen profile based upon the second luminal size parameter and the at least one additional luminal size parameter.

8. The method of claim 7, wherein a length of the stenotic lesion is determined based upon the lumen profile.

9. A device for removing a stenotic lesion from a vessel, the device comprising:
   at least one treatment portion operable to remove at least part of a stenotic lesion; and at least one sizing portion comprising at least one impedance electrode, the at least one sizing portion operable to measure a first luminal size parameter when positioned and operated at a first location and further operable to measure a second luminal size parameter when positioned and operated at a second location;

wherein the device comprises an elongated body selected from the group consisting of a catheter and a wire.

10. The device of claim 9, wherein the at least one treatment portion is selected from the group consisting of a cutting balloon, a cryoplasty device, a rotational atherectomy device, a laser angioplasty device, a vibrating catheter, and a vibrating drill.

11. The device of claim 9, wherein the at least one sizing portion comprises at least one non-impedance sensor in addition to or in lieu of the at least one impedance electrode.

12. The device of claim 9, wherein the at least one treatment portion comprises a balloon, wherein the at least one sizing portion is positioned within the balloon, and wherein the at least one sizing portion is operable to measure at least one luminal parameter within the balloon at one or more stages of balloon inflation.

13. The device of claim 9, further comprising:
at least one suction/infusion port in communication with at least one lumen of the device, said suction/infusion port operable to facilitate one or more fluid injections into a treatment site; and
at least one fluid delivery source operably coupled to the at least one lumen of the device, whereby one or more fluids may be injected from the at least one fluid delivery source through the at least one lumen of the device, through the at least one suction/infusion port, and into the treatment site.

14. A method of removing a stenotic lesion from a vessel, comprising the steps of:
positioning a device within a vessel lumen, the device comprising at least one sizing portion and at least one treatment portion;
operating the at least one sizing portion to obtain a luminal size parameter data value;
operating the at least one treatment portion at a location within the vessel lumen at a stenotic lesion, whereby operation of the at least one treatment portion is performed in connection with the luminal size parameter data value, and whereby operation of the at least one treatment portion increases the luminal size parameter data value; and
ceasing operation of the at least one treatment portion when the luminal size parameter data indicates a preferred luminal size parameter;
wherein the device is configured for operation with a data acquisition and processing system operably coupled thereto, the data acquisition and processing system operable to receive conductance data from the at least one sizing portion and further operable to calculate the at least one luminal size parameter data value based upon said conductance data.

15. The method of claim 14, wherein the preferred luminal size parameter comprises a preferred luminal size parameter range, and wherein the ceasing operation step is performed when the luminal size parameter data is within the preferred luminal size parameter range.

16. The method of claim 14, further comprising the steps of:
selecting an appropriately-sized stent based at least in part upon the preferred luminal size parameter; and
implanting the stent into the vessel lumen.

17. The method of claim 14, wherein the luminal size perimeter data comprises a first luminal size parameter obtained at a first location within the vessel lumen, a second luminal size parameter obtained at a second location within the vessel lumen, and at least one then-current luminal size parameter obtained after initial operation of the at least one treatment portion.

18. The method of claim 17, wherein the first luminal size parameter is selected from the group consisting of a first luminal diameter and a first cross-sectional area, and wherein the second luminal size parameter is selected from the group consisting of a second luminal diameter and a second cross-sectional area.

* * * * *